United States Patent [19]

Mayer-Mader et al.

[11] 4,032,541

[45] June 28, 1977

[54] XANTHOGEN DISULPHIDES WITH FUNCTIONAL GROUPS

[75] Inventors: Rudolf Mayer-Mader; Wilhelm Göbel, both of Cologne, Germany

[73] Assignee: Bayer Aktiengesellschaft, Germany

[22] Filed: Sept. 20, 1976

[21] Appl. No.: 724,288

Related U.S. Application Data

[62] Division of Ser. No. 570,098, April 21, 1975, which is a division of Ser. No. 440,014, Feb. 6, 1974, Pat. No. 3,926,912.

[30] Foreign Application Priority Data

Feb. 10, 1973 Germany ........................ 2306610
May 23, 1973 Germany ........................ 2352937

[52] U.S. Cl. ................................. 260/340.9
[51] Int. Cl.² ............................. C07D 317/00
[58] Field of Search ........................ 260/340.9

[56] References Cited

UNITED STATES PATENTS 3,954,916  5/1976  Mayer-Mader et al. ............ 260/888

FOREIGN PATENTS OR APPLICATIONS 2,306,610  8/1974  Germany ........................ 260/340.7

Primary Examiner—Ethel G. Love
Attorney, Agent, or Firm—Connolly and Hutz

[57] ABSTRACT

This invention relates to xanthogen disulphides of the formula

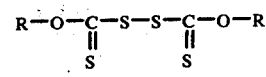

in which R is the same or different and denotes the following groups:

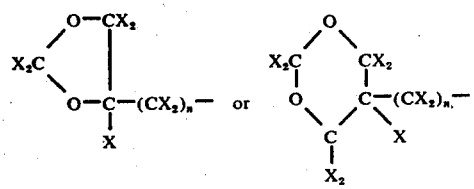

wherein
X = H, alkyl, aryl, aralkyl or halogen
$n$ = 1 to 20, a process for preparing them, a process for polymerising dienes and α-olefines in the presence of these particular xanthogen disulphides and to vulcanizable rubber mixtures consisting of an uncross-linked benzene soluble chloroprene homopolymer or copolymer which is prepared in the presence of said xanthogen disulphides.

2 Claims, No Drawings

XANTHOGEN DISULPHIDES WITH FUNCTIONAL GROUPS

CROSS-REFERENCE TO RELATED APPLICATIONS

This application is a division of application Ser. No. 570,098 filed Apr. 21, 1975 which, in turn, is a division of application Ser. No. 440,014 filed Feb. 6, 1974 and now U.S. Pat. No. 3,926,912.

This invention relates to certain xanthogen disulphides with functional groups, a process for preparing them, a process for polymerising dienes and α-olefines in the presence of these particular xanthogen disulphides and to vulcanisable rubber mixtures consisting of an uncross-linked benzene soluble chloroprene homopolymer or copolymer which is prepared in the presence of said xanthogen disulphides.

Xanthogen disulphides of this invention have the general formula I

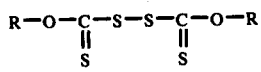

in which R is the same or different and denotes the following groups:

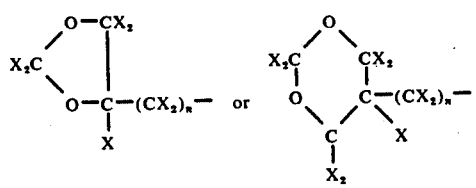

wherein
X = H, alkyl, aryl, aralkyl or halogen
n = 1 to 20;
alkyl groups containing 1 to 6 carbon atoms (methyl, ethyl, isopropyl, hexyl), phenyl, naphthyl, benzyl, chlorine, bromine and iodine being preferred.

The invention particularly relates to those xanthogen disulphides of the general formula I in which the two groups R are identical and the groups X denotes hydrogen or alkyl (preferably $C_1$ $C_6$).

Another object of this invention is a process for producing xanthogen disulphides of formula I wherein an alcohol of the formula ROH has the meaning indicated above is reacted with carbon disulphide in the presence of a strong alkali to form the alkali metal xanthate which is then oxidized to the xanthogen disulphide. Alcohols with the following groups R are particularly suitable for this process:

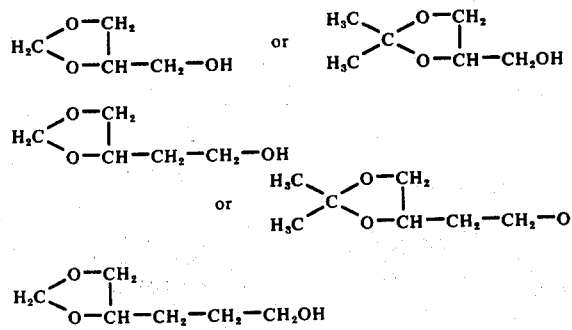

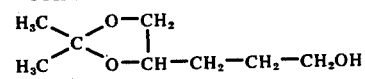

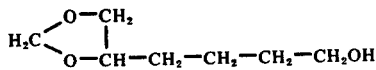

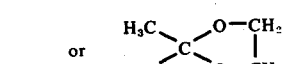

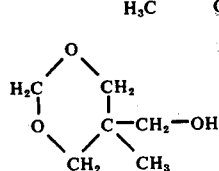 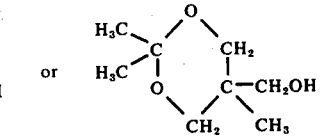

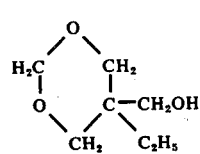 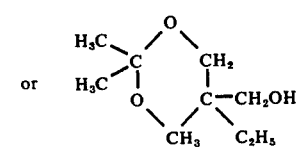

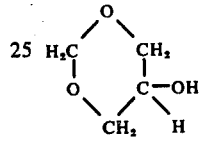

The process is generally carried out as follows: Starting from an aqueous solution of an alkali, e.g. a 20 – 50% aqueous potassium or sodium hydroxide solution, approximately equimolar quantities of an alcohol ROH (in which R has the meaning defined above) are added. Carbon disulphide is slowly added to this mixture. The carbon disulphide may be added in equimolar quantities or in an excess. An exothermic reaction immediately sets in to form the xanthate. During this reaction, the mixture is cooled so that the reaction temperature does not rise above 50° C.

The reaction may be represented as follows:

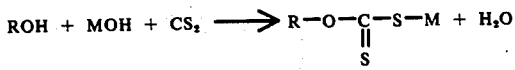

in which
M = alkali metal and R has the meaning defined above.

The aqueous xanthate solution obtained is then oxidesed to xanthogen disulphide by the addition of a suitable oxidising agent such as hydrogen peroxide or potassium peroxydisulphate (as aqueous solution). The water-insoluble xanthogen disulphide precipitates. It is separated from the aqueous phase, e.g. by filtration or decanting, and dried. The reaction may be represented as follows:

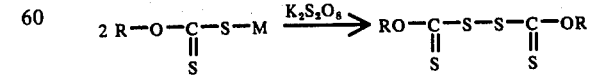

R has the meaning defined above.

This process is carried out similar to the process for producing dialkyl xanthogen disulphides as described, for example, in Kirk-Othmer, "Encyclopedia of Chemical Technology", 2nd Edition, Vol. 22 (1970), pages 419 – 429 and in Ullmann "Encyclopedie der Techn. Chemie" Vol. 18 (1967) pages 718 – 728.

Another object of this invention is a process for polymerising one or more conjugated diolefines and copolymerising one or more conjugated diolefines with α-olefines in the presence of radical forming initiators, in the presence of xanthogen disulphides of the general formula I as molecular weight modifiers. Particularly suitable conjugated diolefines are those which contain 4 to 8 carbon atoms such as butadiene, isoprene, piperylene, chloroprene and 2,3-dichlorobutadiene.

In more detail this invention relates to a process for producing chloroprene polymers which are easy to process, wherein a. 60 to 100 parts by weight of chloroprene and 40 to 0 parts by weight of a diene in which the hydrogen atoms may be partly or completely substituted by halogen atoms and/or of an α-olefine are polymerised in the presence of 0.05 to 30 parts by weight, preferably 0.15 to 5 parts by weight and especially 0.15 to 1 parts by weight of a xanthogen disulphide of the formula I in aqueous dispersion.

The α-olefines used are preferably acrylonitrile, styrene and ethylacrylate. These comonomers are usually present in quantities of up to 40% by weight, based on the diolefine. Suitable radical forming polymerisation catalysts are, for example, peroxides and azo compounds or so-called redox systems. The following are examples: Cumene hydroperoxide, pinene hydroperoxide, potassium peroxidisulphate, tert.-butyl peroxide, azo-bis-isobutyronitrile. Redox systems are: peroxides, e.g. cumene hydroperoxide, in combination with reducing compounds, e.g. formaldehyde sulphoxylate, iron salts or formamidine sulphinic acid.

The polymerisation is preferably carried out in aqueous emulsion. An aqueous emulsifier solution starting from an "aqueous phase" which contains at least 0.1 to 5% by weight of an emulsifier is provided. Suitable emulsifiers are e.g. alkali metal alkyl sulphonates, alkali metal sulphates, long chain carboxylic acids, resinic acids and polyether alcohols. The monomer or monomers together with 0.05 to 30% by weight, preferably 0.15 to 1% by weight, based on the monomers, of a dialkylxanthogen disulphide of formula I are then emulsified in this "aqueous phase" and the radical forming initiator is added. Polymerisation is preferably carried out at temperatures of from −50° to 100° C, preferably 5° to 50° C. This process is basically known for polymerising chloroprene, e.g. from U.S. Pat. Nos. 3,042,652; 3,147,317 and 3,147,318.

When 50 to 100%, preferably 50 to 70% of the monomers have been polymerised, unreacted monomer is removed and then the polymer is recovered from the aqueous emulsion by electrolyte precipitation of freezing coagulation and drying. In this polymerisation the xanthogen disulphide of formula I act as molecular weight modifiers, i.e. they reduce the molecular weight of the resulting polymers compared with the molecular weight of polymers obtained in the absence of xanthogen disulphide. This becomes apparent by comparing the Mooney viscosities of the resulting products.

The xanthogen disulphides of formula I are particularly suitable for modifying the molecular weight of chloroprene polymers. Chloroprene polymers obtained in their presence yield vulcanisates of improved mechanical properties.

This is particularly pronounced in mixtures of uncross-linked benzene soluble polychloroprenes made in accordance with this invention and benzene insoluble, slightly cross-linked polychloroprenes. These mixtures are easy to process and their vulcanisates have particularly high tensile strength.

The tensile strength of these vulcanised polymers can be even further improved by vulcanising in the presence of agents, such as masked diisocyanates, which react with the end groups of the xanthogen disulphides.

Another object of this invention is therefore a mixture of an uncross-linked, benzene soluble chloroprene polymer (a) made from chloroprene and optionally up to 40% by weight (based on the monomer mixture) of an α-olefine in the presence of 0.05 – 30% by weight (based on the monomers) of a xanthogen disulphide of formula I and a cross-linked, benzene insoluble chloroprene polymer (b).

The benzene soluble chloroprene polymer (a) in this mixture is the product described above.

In more detail this invention relates to a process for producing chloroprene polymer mixtures which are easy to process wherein a. 60 to 100 parts by weight of chloroprene and 40 to 0 parts by weight of a diene in which the hydrogen atoms may be partly or completely substituted by halogen atoms and/or of an α-olefine are polymerised in the presence of 0.05 to 30 parts by weight, preferably 0.15 to 5 parts by weight and especially 0.15 to 1 parts by weight of a xanthogen disulphide of the formula I in aqueous dispersion to produce an uncross-linked, benzene soluble polymer which is then mixed with b. a cross-linked, benzene insoluble chloroprene homopolymer or copolymer consisting of 80 to 100 parts by weight of chloroprene and 20 to 0 parts by weight of a divinyl compound and/or an α-olefine, the components A and B being mixed in a ratio by weight of between 20 : 1 and 1 : 20, preferably between 1 : 1 and 7 : 1.

The invention relates also to mixtures of 5 to 95 parts by weight, preferably 55 to 90 parts by weight of an uncross-linked, benzene soluble chloroprene homopolymer or copolymer consisting of 60 to 100 parts by weight of chloroprene and 40 to 0 parts by weight of a diene in which the hydrogen atoms may be partly or completely replaced by halogen atoms and/or of an α-olefine which has been prepared in the presence of 0.05 to 30 parts by weight, preferably 0.15 to 5 parts by weight and especially 0.15 to 1 part by weight of a xanthogen disulphide of formula I and 95 to 5 parts by weight, preferably 45 to 10 parts by weight, of a cross-linked, benzene insoluble chloroprene homopolymer or copolymer of 80 to 100 parts by weight of chloroprene and 20 to 0 parts by weight of a divinyl compound and/or an α-olefine.

Suitable benzene insoluble cross-linked chloroprene polymers can be prepared by various methods which yield cross-linked polymer in the latex form, for example the chloroprene may be polymerised to a high degree of conversion in the absence of a chain transfer agent or with only small quantities of such agent, e.g. an alkylmercaptan or dialkylxanthogen disulphide. A suitable method of carrying out such a process to a high degree of polymerisation has been described, for example in U.S. Pat. No. 3,147,317. In another method of making cross-linked chloroprene polymer a comonomer which is capable of copolymerising with the chloroprene and which contains two or more polymerisable double bonds is added in the polymerisation. Comonomers suitable for this purpose are, for example, divinylbenzene and esters of methacrylic acid and polyhydroxy compounds such as alkylene glycols, dihydroxybenzene or trimethylpropane.

Cross-linked chloroprene polymers are obtained by the same methods as known for making benzene soluble chloroprene polymers but monomer conversion is raised to, e.g. 90 to 100%.

In another method of preparing suitable cross-linked chloroprene polymers the latex of an uncross-linked chloroprene polymer is subjected to a post-treatment which effects cross-linking. Such post-treatment is e.g. irradiation according to U.S. Pat. No. 3,042,652 and treatment with an organic peroxy compound according to U.S. Pat. No. 3,147,318.

In the cross-linked polymer part of the chloroprene, up to about 20% can be replaced by another monomer. Suitable comonomers are the same as with the benzene soluble polymers described above.

The benzene insoluble chloroprene polymer is preferably a copolymer of chloroprene and 2 to 20% by weight (based on chloroprene) of a diester of a dihydric aliphatic alcohol and an acrylic acid. These diesters have the general formula $$H_2C=C-C-O-X-O-C-C=CH_2 \atop {\phantom{H_2C=}|\phantom{-C-}\|\phantom{-O-X-O-}\|\phantom{-C}| \atop \phantom{H_2C=}R_1\phantom{-C-}O\phantom{-O-X-O-}O\phantom{-C}R_2}$$  II in which $R_1$ to $R_2$ represent hydrogen, alkyl containing 1 to 4 carbon atoms or chlorine and X represents an alkylene group containing 2 – 20 carbon atoms.

The following are examples of such compounds: ethylene dimethacrylate, propylene dimethacrylate, butylene dimethacrylate, isobutylene dimethacrylate, ethylene diacrylate, propylene diacrylate, butylene diacrylate and isobutylene diacrylate.

These products are made in accordance with the usual methods of polymerising chloroprene and of copolymerising butadiene and acrylonitrile in aqueous emulsion. The procedure and the products obtained from it are disclosed in British Pat. No. 1,158,970.

The components of the elastomer mixture are preferably combined by vigorously mixing the latices and then recovering the solid polymer mixture by the usual methods, e.g. freezing coagulation (U.S. Pat. No. 2,187,146) or drying on rollers (U.S. Pat. No. 2,914,497). Elektrolyte precipitation is also possible. Alternatively, the components can be recovered individually by the usual methods and then be mixed mechanically, e.g. by kneading on mixing rollers or in an internal mixer such as a Banbury mixer or a Werner-Pfleiderer mixer.

In the case of polychloroprene, the weight ratio of benzene soluble component (a) to cross-linked component (b) may be from 20 : 1 to 1 : 20, preferably from 1 : 1 to 7 : 1. The mixture should contain at least 50 % by weight of benzene soluble component (a).

The polychloroprene mixtures according to the invention can be compounded to form vulcanisable rubber mixtures and vulcanised in the same way as conventional polychloroprenes. They are used for all purposes for which polychloroprenes are suitable.

Their primary advantage is improved processing compared to benzene soluble polychloroprenes and to benzene insoluble polychloroprenes taken along. Compared to known mixtures of benzene soluble and benzene insoluble polychloroprenes, their thermal stability is substantially improved.

When benzene soluble polychloroprenes made in the presence of xanthogen disulphides of formula I are compared to those made in the presence of mercaptans as molecular weight modifiers, they are found to be superior in the tensile strengths of the vulcanisates. The tensile strengths can be even further improved by vulcanising with masked diisocyanates.

EXAMPLES OF THE PREPARATION OF XANTHOGEN DISULPHIDES WHICH CONTAIN ALKOXY GROUPS

A. EXAMPLE 1

Xanthogen disulphide of hexane triol monoacetal

To prepare the xanthogen disulphide of hexane triol monoacetal, 88 g of sodium hydroxide and 90 g of distilled water are introduced into a 3 liter flask and the sodium hydroxide is dissolved with stirring. 292 g of hydroxy-hexane-1,2-diol acetal (hexantriolmonoacetal) of the following formula a $$HO-(CH_2)_4-HC{-O\atop-O}{>}CH_2 \atop {\phantom{HO-(CH_2)_4-H}H_2C-O}$$

are then added and the reaction mixture is stirred for 2 hours. It is then cooled to 10° C and 184 g of carbon disulphide are added dropwise with stirring. The temperature should not rise above 20° C during this operation. When all the carbon disulphide has been added, the whole mixture is stirred for a further 2 hours.

A solution consisting of 300 g of ammonium persulphate and 2 liters of distilled water is then added dropwise to the reaction mixture in which the xanthate has been formed. The xanthogen disulphide which is formed by oxidation is then removed from the aqueous phase, washed with distilled water and taken up in ether, and the ethereal phase is dried with anhydrous sodium sulphate. The solvent is removed in a rotary evaporator. The yield of xanthogen disulphide is 360 g.

$$H_2C{<O-H_2C\atop O-HC}-(CH_2)_4-O-\underset{\underset{S}{\|}}{C}-S-S-\underset{\underset{S}{\|}}{C}-O-$$

$$-(CH_2)_4-CH{-O\atop-O}{>}CH_2 \atop {\phantom{-(CH_2)_4-C}CH_2-O}$$

EXAMPLE 2

Xanthogen disulphide of hexane triol monoketal

To prepare the xanthogen disulphide of hexane triol monoketal, 88 g of sodium hydroxide and 90 g of distilled water are introduced into a 3 liter flask and the sodium hydroxide is dissolved with stirring. 348 g of 6-hydroxy-hexane-1,2-diolmonoketal (hexane triol monoketal of formula b $$\left[HO-(CH_2)_4-HC{-O\atop-O}{>}\underset{CH_3}{\overset{CH_3}{C}} \atop {\phantom{HO-(CH_2)_4-H}H_2C-O}\right]$$

are then added and the mixture then stirred for a further 2 hours. The reaction mixture is then cooled to 10° C and 184 g of carbon disulphide are added dropwise with stirring, during which time the temperature should not rise above 20° C. Stirring is continued for another 2 hours after all the carbon disulphide has been added.

A solution consisting of 300 g of ammonium persulphate and 2 liter of distilled water is then added dropwise into the reaction mixture containing the xanthate which has been formed in the reaction. The xanthogen disulphide obtained by oxidation is then separated from the aqueous phase, washed with distilled water and taken up in ether and the ethereal phase is dried with anhydrous sodium sulphate. The solvent is evaporated in a rotary evaporator. The yield of xanthogen disulphide is 358 g.

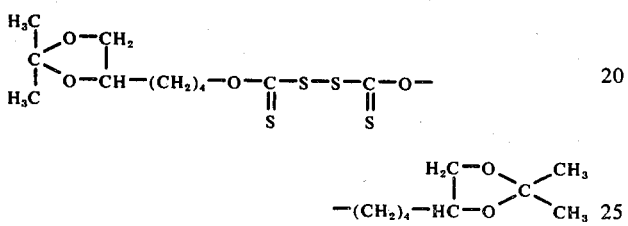

EXAMPLE 3

Xanthogen disulphide of glycerol monoacetals

To prepare xanthogen disulphides of glycerol monoacetals, 88 g of sodium hydroxide and 90 g of distilled water are introduced into a 3 l flask and the sodium hydroxide is dissolved with stirring. 264 g of a mixture of glycerol monoacetals of formulae $C_1$ and $C_2$ which are obtained by reacting glycerol with formaldehyde are then added and stirring is continued for 2 hours.

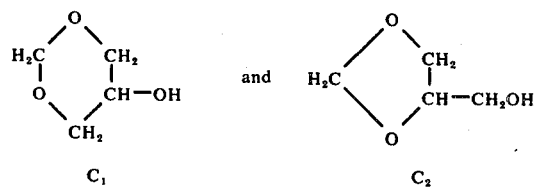

The reaction mixture is then cooled to 10° C. 184 g of carbon disulphide are then added dropwise with stirring; the temperature should not rise above 20° C during this operation. Stirring is continued for 2 hours after all the carbon disulphide has been added.

A solution consisting of 300 g of ammonium persulphate and 2 liters of distilled water is then added dropwise to the reaction mixture of the resulting xanthates. The xanthogen disulphides formed by oxidation are then separated from the aqueous phase, washed with distilled water and taken up with ether and the ethereal phase is dried with anhydrous sodium sulphate. The solvent is removed in a rotary evaporator. The yield of xanthogen disulphides is 250 g.

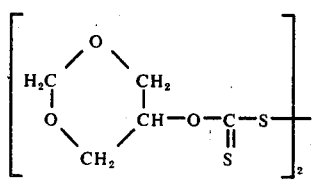

-continued
and

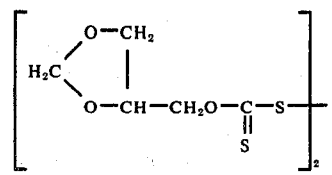

EXAMPLE 4

Xanthogen disulphide of glycerol monoketal

To prepare the xanthogen disulphide of glycerol monoketal, 88 g of sodium hydroxide and 90 g of distilled water are introduced into a 3 liter flask and the sodium hydroxide is dissolved with stirring. 266 g of the glycerol monoketal of formula $d$ are then added.

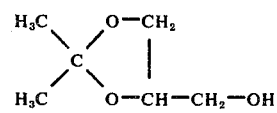

and stirring is continued for 2 hours. The reaction mixture is then cooled to 10° C. 176 g of carbon disulphide are then added with stirring; the temperature should not rise above 20° C during this operation. After all the carbon disulphide has been added, the reaction mixture is stirred for another 2 hours. A solution consisting of 300 g of ammonium persulphate and 2 liters of distilled water is then added dropwise to the reaction mixture containing the resulting xanthate. The xanthogen disulphide obtained by oxidation is then separated from the aqueous phase, washed with distilled water and taken up in either and the ethereal phase is dried with anhydrous sodium sulphate. The solvent is removed in a rotary evaporator. The yield of xanthogen disulphide is 270 g.

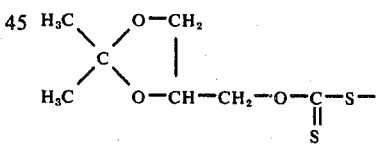

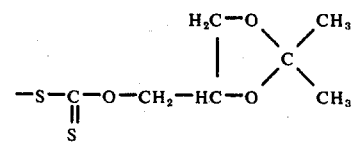

EXAMPLE 5

Xanthogen disulphide of 1,1,1-tris-hydroxymethyl-propane monoacetal

To prepare the xanthogen disulphide of 1,1,1-tris-hydroxy-methyl-propane monoacetal, 88 g of sodium hydroxide and 90 g of distilled water are introduced into a 3 liter flask and the sodium hydroxide is dissolved with stirring. 292 g of the monoacetal of formula $e$

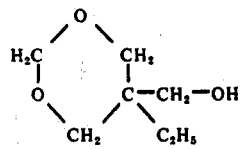

are then added and stirring is continued for 2 hours. The reaction mixture is then cooled to 10° C and 176 g of carbon disulphide are added with stirring. The temperature should not rise above 20° C during the addition of carbon disulphide. The reaction mixture is stirred for another 2 hours after all the carbon disulphide has been added. A solution consisting of 300 g of ammonium persulphate and 2 liters of distilled water is then added dropwise to the reaction mixture containing the resulting xanthate. The xanthogen disulphide obtained on oxidation is then separated from the aqueous phase, washed with distilled water and taken up in ether and the ethereal phase is dried with anhydrous sodium sulphate. The solvent is removed in a rotary evaporator. The yield of xanthogen disulphide is approximately 350 g.

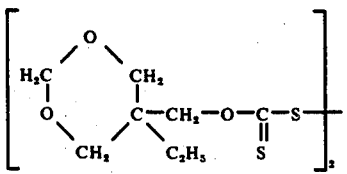

B.

I. Example of Polymerisation

The following phases are prepared separately and introduced into the polymerisation vessel:

Monomer phase 100 parts by weight of chloroprene
y parts by weight of xanthogen disulphide of hexane triol monoacetal

Aqueous phase 120 parts by weight of distilled water
5 parts by weight of sodium salt of a disproportionated abietic acid
0.5 parts by weight of sodium salt of a condensation product of naphthalene sulphonic acid and formaldehyde
0.5 parts by weight of sodium hydroxide
0.5 parts by weight of tetrasodium pyrophosphate
The quantity y of modifier is varied as follows:
$y_1 = 0.5$ parts by weight
$y_2 = 0.75$ parts by weight
$y_3 = 0.80$ parts by weight
$y_4 = 1.00$ parts by weight After mixing the two phases, the temperature is raised to 43° C and polymerisation is initiated by an activator solution consisting of 2.5 parts by weight of formamidine sulphinic acid and 97.5 parts by weight of distilled water. The activator solution is added dropwise as required.

When 65 to 70% of the monomer has been converted to polymer, the remaining monomer is removed by steam distillation and the polymer is isolated from the latex by electrolyte precipitation and dried.

The Mooney viscosities were found to vary with the quantities of modifier as follows:

| y | Regulator % by weight | Mooney-viscosity ML-4'/100° C |
|---|---|---|
| $y_1$ | 0.5 | 130 |
| $y_2$ | 0.75 | 57 |
| $y_3$ | 0.80 | 50 |
| $y_4$ | 1.00 | 32 |

II. Example of polymerisation

The following phases were prepared separately and introduced into the polymerisation vessel:

Monomer phase

100 Parts by weight of chloroprene
z Parts by weight of xanthogen disulphide of 1,1,1-tris-hydroxymethylpropane monoacetal

Aqueous phase

120 Parts by weight of distilled water
5 Parts by weight of sodium salt of a disproportionated abietic acid
0.5 Parts by weight of sodium salt of a condensation product of naphthalene sulphonic acid and formaldehyde
0.5 Parts by weight of sodium hydroxide
0.5 Parts by weight of tetrasodium pyrophosphate
The quantity z of modifier was varied as follows:
$z_1 = 0.1$ Part by weight
$z_2 = 0.5$ Part by weight
$z_3 = 1.0$ Part by weight When the two phases have been mixed, the temperature is raised to 43° C and polymerisation is initiated by an activator solution consisting of 2.5 parts by weight of formamidine sulphinic acid and 97.5 parts by weight of distilled water. The activator solution is added dropwise as required.

When 65 to 70% of the monomer has been converted to polymer, the remaining monomer is removed by steam distillation and the polymer is isolated from the latex by electrolyte precipitation and dried.

The following Mooney viscosities were then measured in dependence on the modifier quantity z:

| z | Regulator % by weight | Mooney viscosity ML-4'/100° C |
|---|---|---|
| $z_1$ | 0.1 | 140 |
| $z_2$ | 0.5 | 92 |
| $z_3$ | 1.0 | 23 |

III. Example of polymerisation (Comparison example)

The following phases were prepared separately and introduced into the polymerisation vessel:

Monomer phase

100 Parts by weight of chloroprene
0.45 Parts by weight of diisopropyl xanthogen disulphide

Aqueous phase

120 Parts by weight of distilled water
5 Parts by weight of sodium salt of a disproportionated abietic acid 0.5 Parts by weight of sodium salt of a condensation product of naphthalene sulphonic acid and formaldehyde
0.5 Parts by weight of sodium hydroxide
0.5 Parts by weight of tetrasodium pyrophosphate When the two phases have been mixed, the temperature is raised to 43° C and polymerisation is released by an activator solution consisting of 2.5 parts by weight of formamidine sulphinic acid and 97.5 parts by weight of distilled water. The activator solution is added dropwise as required.

When 65 to 70% of the monomer has been converted to polymer, the remaining monomer is removed by steam distillation and the polymer is isolated from the latex by electrolyte precipitation and dried. The polymer has a Mooney viscosity of approximately 44.

IV. Example of polymerisation (Comparison example)

The following phases were prepared separately and introduced into the polymerisation vessel:

Monomer phase

100 Parts by weight of chloroprene
0.28 Parts by weight of n-DDM (normal dodecylmercaptan)

Aqueous phase

120 Parts by weight of distilled water
5 Parts by weight of sodium salt of a disproportionated abietic acid
0.5 Parts by weight of sodium salt of a condensation product of naphthalene sulphonic acid and formaldehyde
0.5 Parts by weight of sodium hydroxide
0.5 Parts by weight of tetrasodiumpyrophosphate When the two phases have been mixed, the temperature is raised to 43° C and polymerisation is initiated with an activator solution consisting of 2.5 parts by weight of formamidine sulphinic acid and 97.5 parts by weight of distilled water. The activator solution is added dropwise as required. When 65 to 70% of the monomer has been converted to polymer, the remaining monomer is removed by steam distillation and the polymer is isolated from the latex by electrolyte precipitation and dried. The polymer has a Mooney viscosity of approximately 43.

V. Example of polymerisation (Comparison example)

The following phases were prepared separately and introduced into the polymerisation vessel:

Monomer phase

100 Parts by weight of chloroprene
0.4 Parts by weight of diethyl xanthogen disulphide Aqueous phase 120 Parts by weight of distilled water
5 Parts by weight of sodium salt of a disproportionated abietic acid
0.5 Parts by weight of sodium salt of a condensation product of naphthalene sulphonic acid and formaldehyde
0.5 Parts by weight of sodium hydroxide
0.5 Parts by weight of tetrasodium pyrophosphate When the two phases have been mixed, the temperature is raised to 43° C and polymerisation is initiated with an activator solution consisting of 2.5 parts by weight of formamidine sulphinic acid and 97.5 parts by weight of distilled water. The activator solution is added dropwise as required. When 65 to 70% of the monomer has been converted to polymer, the remaining monomer is removed by a steam distillation and the polymer is isolated from the latex by electrolyte precipitation and dried. The polymer has a Mooney viscosity of approximately 43.

VI. Example of polymerisation (Comparison example)

The following phases were prepared separately and introduced into the polymerisation vessel:

Monomer phase

100 Parts by weight of chloroprene
0.55 Parts by weight of xanthogen disulphide of ethylene glycol monomethylether Aqueous phase 120 Parts by weight of distilled water
5 Parts by weight of sodium salt of a disproportionated abietic acid
0.5 Parts by weight of sodium salt of a condensation product of naphthalene sulphonic acid and formaldehyde
0.5 Parts by weight of sodium hydroxide
0.5 Parts by weight of tetrasodium pyrophosphate When the two phases have been mixed, the temperature is raised to 43° C and polymerisation is initiated with an activator solution which consists of 2.5 parts by weight of formamidine sulphinic acid and 97.5 parts by weight of distilled water. The activator solution is added dropwise as required. When 65 to 70% of the monomer has been converted to polymer, the remaining monomer is removed by steam distillation and the polymer is isolated from the latex by electrolyte precipitation and dried. The polymer has a Mooney viscosity of approximately 43.

VII. Example of polymerisation (Comparison example)

The following phases were prepared separately and introduced into the polymerisation vessel:

Monomer phase

100 Parts by weight of chloroprene
0.55 Parts by weight of xanthogen disulphide of ethylene glycol monoethyl ether
0.35 Parts by weight of sulphur Aqueous phase 120 Parts by weight of distilled water
5 Parts by weight of sodium salt of a disproportionated abietic acid
0.7 Parts by weight of sodium salt of a condensation product of naphthalene sulphonic acid and formaldehyde
0.8 Parts by weight of sodium hydroxide
0.5 Parts by weight of tetrasodium pyrophosphate When the two phases have been mixed, the temperature is raised to 43° C and polymerisation is initiated with an activator solution which has the following composition: 1.3 Parts of distilled water, 0.04 parts of potassium persulphate and 0.04 parts of anthraquinone sulphonic acid sodium salt. The activator solution is added as required. When between 65 and 95% of the monomer (depending on the desired viscosity) has been converted to polymer, the remaining monomer is removed by steam distillation and the polymer is isolated by electrolyte precipitation and dried.

VIII. Example of polymerisation (Comparison example)

The following phases were prepared separately and introduced into the polymerisation vessel:

Monomer phase

100 Parts by weight of chloroprene
0.4 Parts by weight of xanthogen disulphide of ethanol
0.35 Parts by weight of sulphur

Aqueous phase

120 Parts by weight of distilled water
5 Parts by weight of sodium salt of a disproportionated abietic acid
0.7 Parts by weight of sodium salt of a condensation product of naphthalene sulphonic acid and formaldehyde
0.8 Parts by weight of sodium hydroxide
0.5 Parts by weight of tetrasodium pyrophosphate When the two phases have been mixed, the temperature is raised to 43° C and polymerisation is initiated with an activator solution of the following composition: 1.3 Parts of distilled water, 0.04 parts of potassium persulphate and 0.04 parts of anthraquinone sulphonic acid sodium salt. The activator solution is added as required. When between 65 and 95% of the monomer (depending on the desired viscosity) has been converted to polymer, the remaining monomer is removed by steam distillation and the polymer isolated by electrolyte precipitation and dried.

IX. Example of polymerisation

The following phases are prepared separately and introduced into the polymerisation vessel:

Monomer phase

100 Parts by weight of chloroprene
0.85 Parts by weight of xanthogen disulphide of hexanetriol monoacetal
0.35 Parts by weight of sulphur

Aqueous phase

120 Parts by weight of distilled water
5 Parts by weight of sodium salt of a disproportionated abietic acid
0.7 Parts by weight of sodium salt of a condensation product of naphthalene sulphonic acid and formaldehyde
0.8 Parts by weight of sodium hydroxide
0.5 Parts by weight of tetrasodium pyrophosphate When the two phases have been mixed, the temperature is raised to 43° C and polymerisation is initiated with an activator solution of the following composition:

1.3 Parts of distilled water, 0.04 parts of potassium persulphate and 0.04 parts of anthraquinone sulphonic acid sodium salt. The activator solution is added as required. When between 65 and 95% of the monomer (depending on the desired viscosity) has been converted to polymer, the remaining monomer is removed by steam distillation and the polymer is isolated by electrolyte precipitation and dried.

The polymers prepared under I – IX are then mixed with the following components on rollers in the usual manner:

Formulation ($\alpha$)

100 Parts by weight of polychloroprene
29 Parts by weight of inactive carbon black
0.5 Parts by weight of stearic acid
2.0 Parts by weight of phenyl-$\beta$-naphthylamine
4.0 Parts by weight of magnesium oxide
5.0 Parts by weight of zinc oxide
0.5 Parts by weight of ethylene thiourea

Formulation ($\alpha$)

100 Parts by weight of polychloroprene
29 Parts by weight of inactive carbon black
0.5 Parts by weight of stearic acid
2.0 Parts by weight of phenyl-$\alpha$-naphthylamine
1.0 Parts by weight of magnesium oxide
5.0 Parts by weight of zinc oxide
3.0 Parts by weight of TA-11 (R)

Vulcanization is carried out at 151° C for 30 minutes. The vulcanizates obtained have the properties shown below (Table 1). It can be seen from Table 1 that the highest strength values are obtained when regulators in the form of the particular xanthogen disulphides of formula K are used (Example I) Formulation $\alpha$. The difference is particularly marked when using a vulcanization accelerator which responds to the modified xanthogen disulphides of Formula I (Example I) Formulation $\beta$.

(R) = Vulcanization accelerator of Du Pont

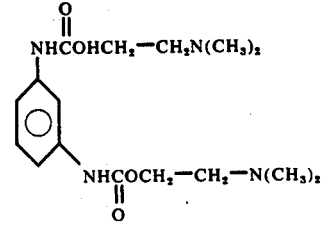

Table 1

|  | Example I | Example III | Example IV | Example V | Example VI |
|---|---|---|---|---|---|
| Formulation ($\alpha$) | | | | | |
| Tensile strength (kg/cm²) | 159 | 143 | 145 | 144 | 142 |
| Elongation at break (%) | 630 | 640 | 615 | 680 | 650 |
| Modulus (300% elongation) kg/cm² (500% elongation) | 48/123 | 43/107 | 42/112 | 45/105 | 48/111 |
| Hardness RT | 57 | 55 | 53 | 58 | 57 |
| Elasticity | 56 | 54 | 52 | 56 | 54 |
| Formulation ($\beta$) | | | | | |
| Tensile strength (kg/cm² | 177 | — | 115 | — | — |
| Elongation at break (%) | 870 | — | 925 | — | — |
| Modulus (300% elongation) kg/cm² (500% elongation) | 37/92 | — | 18/44 | — | — |
| Hardness RT | 37 | — | 48 | — | — |
| Elasticity | 30 | — | 53 | — | — |

X. Example of Polymerisation

A.

Preparation of the benzene insoluble polychloroprene as one of the components for preparing a mixture which has good properties for working up.

The following components are introduced into a 40 liter autoclave which is equipped with stirrer, thermometer and feed tubes and connected to a cooling system:

14.4 l of salt-free water, 815 g of the sodium salt of a disproportionated abietic acid mixture, 72 g of a condensation product of an alkyl naphthalene sulphonic acid and formaldehyde, 36 g of sodium hydroxide, and 60 g of tetrasodium pyrophosphate. A solution containing the following constituents is then added: 10.620 g of chloroprene, 1.380 g of ethylene glycol dimethacrylate, 34 g of n-dodecylmercaptan. The reaction mixture is then heated to 43° C and polymerisation is initiated by dropwise addition of a catalyst solution containing the following components:

2.5 g of formamidine sulphinic acid, dissolved in 97.5 g of distilled water. When approximately 80% of the monomer has been polymerised, polymerisation is stopped by the addition of a stabilizer solution of the following composition:

5 g of phenothiazine, and 5 g of p-tert.-butyl-pyrocatechol in 500 g of toluene. The latex is then freed from unreacted monomer.

B.

Preparation of benzene soluble polychloroprene as one of the components for the preparaton of a mixture which has good properties for working up.

Preparation of the benzene soluble polychloroprene is carried out in accordance with polymerisation examples I, IV, V and VI.

XI. Preparation of a mixture of benzene soluble and benzene insoluble polychloroprene 85 Parts by weight of benzene soluble polymer component are mixed with 15 parts by weight of benzene insoluble polymer component (X) in the latex and the polymer is then isolated from the latex (Table II).

Table II

| XI | Benzene soluble polychloroprene 85 Parts by weight | Benzene insoluble polychloroprene 15 parts by weight |
|---|---|---|
| A | Polymer Example I | Polymer Example X |
| B | Polymer Example IV | Polymer Example X |
| C | Polymer Example V | Polymer Example X |
| D | Polymer Example VI | Polymer Example X |

Polymers XI A to XI D are then mixed in accordance with Formulation α and Formulation β and vulcanized at 151° C for 30 minutes.

I. PREPARATION OF UNCROSS-LINKED, BENZENE SOLUBLE CHLOROPRENE POLYMERS.

EXAMPLE 6

Monomer phase 100.00 Parts by weight of chloroprene
0.85 Parts by weight of xanthogen disulphide of the following formula

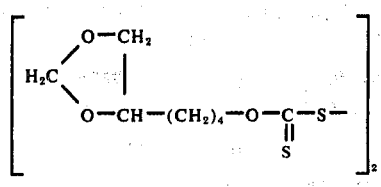

Aqueous phase 120.0 Parts by weight of salt-free water
5.0 Parts by weight of sodium salt of a disproportionated abietic acid
0.5 Parts by weight of sodium salt of a condensation product of naphthalene sulphonic acid and formaldehyde
0.5 Parts by weight of sodium hydroxide
0.5 Parts by weight of tetrasodium pyrophosphate When the two phases have been mixed, the temperature is adjusted to 43° C and polymerisation is initiated with an activator solution consisting of 2.5 parts by weight of formamidine sulphinic acid and 97.5 parts by weight of salt-free water. The activator solution is added dropwise as required.

When 65 to 70% of the monomers have been polymerised, polymerisation is stopped by the addition of a radical acceptor, e.g. tertiary butyl pyrocatechaol, and the remaining monomers are removed by steam distillation. The Mooney viscosity ML-4'/100° C of a sample which has been isolated by electrolyte precipitation and drying is 45.

EXAMPLE 7

Monomer phase 100.00 Parts by weight of chloroprene
0.84 parts by weight of xanthogen disulphide of the following formula

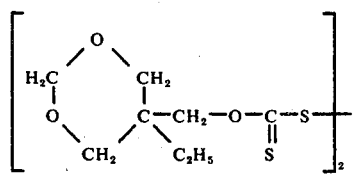

Aqueous phase 120.0 Parts by weight of salt-free water
5.0 Parts by weight of sodium salt of a dispropionated abietic acid
0.5 Parts by weight of sodium salt of a condensation product of naphthalene sulphonic acid and formaldehyde
0.5 Parts by weight of sodium hydroxide
0.5 Parts by weight of tetrasodium pyrophosphate When the two phases have been mixed, the temperature is adjusted to 43° C and polymerisation is initiated with an activator solution consisting of 2.5 parts by weight of formamidine sulphinic acid and 97.5 parts by weight of salt-free water. The activator solution is added dropwise as required.

When 65 to 70% of the monomers have been converted to polymer, polymerisation is stopped by the addition of a radical acceptor, e.g. tertiary butyl pyrocatechol, and the remaining monomers are removed by steam distillation. The Mooney viscosity ML-4'/100° C of a sample which has been isolated by electrolyte precipitation and drying is 45.

EXAMPLE 8 (Comparison Example)

Monomer phase 100.00 Parts by weight of chloroprene
0.28 Parts by weight of n-dodecylmercaptan Aqueous phase 120.0 Parts by weight of salt-free water
5.0 Parts by weight of sodium salt of a disproportionated abietic acid
0.5 Parts by weight of sodium salt of a condensation product of naphthalene sulphonic acid and formaldehyde
0.5 parts by weight of sodium hydroxide
0.5 Parts by weight of tetrasodium pyrophosphate Polymerisation is carried out as in Example 1 and 2. The Mooney viscosity ML-4'/100° C of the resulting polymer is 45.

EXAMPLE 9 (Comparison Example)

Example 4 is similar to Example 3 except that instead of 0.28 parts by weight of n-dodecylmercaptan, 0.4 parts by weight of diethylxanthogen disulphide are used. The Mooney-viscosity ML-4'/100° C of the resulting polymer is 45.

II. Preparation of cross-linked, benzene insoluble polychloroprene

EXAMPLE 10

The following components are introduced into a 40 liter autoclave which is equipped with stirrer, thermometer, feed tubes and a cooling system:

14.4 kg of salt free water
0.815 kg sodium salt of a disproportionated abietic acid
0.072 kg sodium salt of a condensation product of alkyl naphthalene sulphonic acid and formaldehyde
0.036 kg sodium hydroxide
0.060 kg tetrasodium pyrophosphate When these components have been thoroughly mixed, the following are added:

10.620 kg of chloroprene
1.380 kg ethylene glycol dimethacrylate
0.034 kg n-dodecylmercaptan The autoclave contents are then heated to 43° C and polymerisation is initiated with dropwise addition of a catalyst solution containing 2.5 g of formamidine sulphinic acid dissolved in 97.5 g of salt-free water.

When approximately 80% of the monomers have been converted to polymer, polymerisation is stopped by the addition of a stabilizer solution of 5 g of phenothiazine,
5 g of p-tert.-butyl pyrocatechol,
500 g of toluene.

The latex is then freed from unreacted monomers by steam distillation. The Mooney viscosity ML-4'/100° C of the polymer is 70.

III Preparation of mixtures of uncross-linked and cross-linked polychloroprene

EXAMPLE 11–18

In each of Examples 6 – 9, 55 parts by weight (based on the solids content) of the polymer latices of Examples 1 to 4 are mixed with 45 parts by weight (based on the solids content) of the polymer latex from Example 5, precipitated by freeze coagulation and dried.

In each of Examples 10 –13, 85 parts by weight, (based on the solids content) of the polymer latices of Examples 1 – 4 are mixed with 15 parts by weight (based on the solids content) of the polymer latex from Example 5, precipitated by freeze coagulation and dried.

The polymer mixtures of Examples 6 to 13 are then mixed with the following components on rollers in the usual manner:

100.0 Parts by weight polymer mixture
29.0 Parts by weight inactive carbon black
0.5 Parts by weight stearic acid
2.0 Parts by weight phenyl-$\beta$-naphthylamine
4.0 Parts by weight magnesium oxide
5.0 Parts by weight zinc oxide
0.5 Parts by weight ethylene thiourea.

The mixtures are vulcanized at 150° C for 30 minutes. The vulcanizate obtained in this way have the properties shown in Table I.

The results demonstrate convincingly that the highest strengths are obtained when the mixtures contain polymers which have been prepared using the particular xanthogen disulphides.

Table I

| | Examples | | | | | | | |
|---|---|---|---|---|---|---|---|---|
| | 11 | 12 | 13 | 14 | 15 | 16 | 17 | 18 |
| Tensile strength (kp/cm$^2$) DIN 53504 | 121 | 122 | 109 | 115 | 140 | 153 | 130 | 133 |
| Elongation at break (%) DIN 53504 | 445 | 455 | 445 | 450 | 560 | 585 | 585 | 550 |
| Modulus (300% elongation in kp/cm$^2$) DIN 53504 | 63 | 60 | 55 | 57 | 54 | 59 | 41 | 48 |
| Shore hardness A at RT DIN 53505 | 58 | 57 | 56 | 56 | 57 | 56 | 53 | 54 |
| Elasticity DIN 53512 | 54 | 54 | 50 | 51 | 56 | 55 | 52 | 53 |

We claim:

1. An xanthogen disulphide of the formula

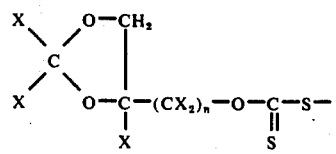

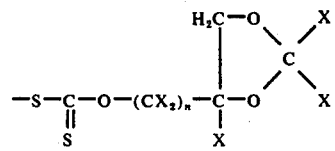

wherein X may be the same or different and is selected from the group consisting of hydrogen, alkyl having 1 to 6 carbon atoms, phenyl, naphthyl, benzyl, chlorine, bromine and iodine and each n is an integer of from 1 to 20.

2. The xanthogen disulphide of claim 1 wherein the X groups are hydrogen or alkyl having 1 to 6 carbon atoms.

* * * * *